(12) United States Patent
Kim

(10) Patent No.: US 11,534,201 B2
(45) Date of Patent: Dec. 27, 2022

(54) ARTIFICIAL INTELLIGENCE-BASED CANNULA SURGERY DIAGNOSTIC DEVICE

(71) Applicant: 365MC NETWORKS, Seoul (KR)

(72) Inventor: Nam Chul Kim, Seoul (KR)

(73) Assignee: 365MC NETWORKS, Seoul (KR)

( * ) Notice: Subject to any disclaimer, the term of this patent is extended or adjusted under 35 U.S.C. 154(b) by 922 days.

(21) Appl. No.: 16/389,397

(22) Filed: Apr. 19, 2019

(65) Prior Publication Data

US 2020/0138476 A1  May 7, 2020

(30) Foreign Application Priority Data

Nov. 7, 2018  (KR) ........................ 10-2018-0135636

(51) Int. Cl.
| | |
|---|---|
| *A61B 17/34* | (2006.01) |
| *A61B 34/20* | (2016.01) |
| *A61B 90/00* | (2016.01) |
| *A61B 34/30* | (2016.01) |
| *A61B 34/10* | (2016.01) |

(52) U.S. Cl.
CPC .......... *A61B 17/3421* (2013.01); *A61B 34/20* (2016.02); *A61B 90/37* (2016.02); *A61B 34/30* (2016.02); *A61B 2034/104* (2016.02); *A61B 2034/2048* (2016.02)

(58) Field of Classification Search
CPC ..... A61B 17/3421; A61B 34/20; A61B 90/37; A61B 34/30; A61B 2034/104; A61B 2034/2048; A61B 17/3403; A61B 17/3415; A61B 2034/107; A61B 2034/101; A61B 2034/2065; A61B 2034/2074; A61B 2090/364; A61B 34/10; A61B 2017/00119; A61B 2034/2059; G06N 20/00
See application file for complete search history.

(56) References Cited

U.S. PATENT DOCUMENTS

| | | | |
|---|---|---|---|
| 2004/0073195 A1* | 4/2004 | Cucin | A61B 17/32002 604/542 |
| 2005/0027281 A1* | 2/2005 | Lennox | A61F 7/12 604/508 |
| 2019/0192768 A1* | 6/2019 | Gupta | G16H 40/63 |

FOREIGN PATENT DOCUMENTS

| | | | |
|---|---|---|---|
| KR | 10-2012-0047896 A | 5/2012 | |
| KR | 10-2012-0115486 A | 10/2012 | |
| WO | WO-2018175945 A1 * | 9/2018 | A61J 1/2096 |

* cited by examiner

*Primary Examiner* — Tracy Y. Li
(74) *Attorney, Agent, or Firm* — Paratus Law Group, PLLC

(57) ABSTRACT

Disclosed is an artificial intelligence-based cannula surgery diagnostic device. The device includes a cannula stroke sensing unit for sensing a stroke of a cannula generated in a surgical procedure of a patient; a surgical data processing unit for receiving surgical data generated based on a stroke of the cannula; and a surgical prognostic information-generating unit for analyzing the received surgical data based on the existing learned surgical data to generate surgical prognostic information for the patient.

6 Claims, 3 Drawing Sheets

ARTIFICIAL INTELLIGENCE-BASED CANNULA SURGERY DIAGNOSTIC DEVICE

CROSS-REFERENCE TO RELATED APPLICATION

This application claims priority to and the benefit of Korean Patent Application No. 10-2018-0135636 filed on Nov. 7, 2018, which is hereby incorporate by reference in its entirety.

BACKGROUND

Field of the Invention

The present invention relates to an artificial intelligence-based cannula surgery diagnostic technique, and more specifically, it relates to an artificial intelligence-based cannula surgery diagnostic device capable of predicting a surgical result based on movement of a cannula and informing an erroneous movement in real time.

Related Art

Since liposuction is a procedure in which a practitioner maintains a high level of concentration during manipulation of a subject and manipulates the surgical device or directly operates for the entire duration of the procedure by using the surgical instrument, it causes serious fatigue of practitioner. And, there are problems in that surgical accidents such as hemorrhage, muscle rupture, etc., are increased due to a decreased concentration due to a long time surgical procedure, and the side effects of the patient are increased due to this. In addition, since in the liposuction it is difficult to know the result in the format of data after the end of the surgical procedure, there is also the problem that it is difficult to make a perfect post-care because it prescribes the general post-care method instead of the post-management method according to each result of the surgical procedure.

Korean Patent Laid-Open No. 10-2012-0047896 (2012 May 14) relates to a delivery device having sensor and one or more cannulas in which the device provides a base part which can have at least one cannula disposed subcutaneously or can be connected thereto, wherein the base part comprises a contact surface or mounting surface for securing the base part to the patient's skin, a securing means connecting supply drugs etc., to the base part, and a sensor and/or transmitter unit, wherein at least one cannula is attached to or is provided with a retraction means, the retraction means can remove at least one cannula from a subcutaneous use position, and the cannula can be retracted to a position that is not engaged with the patient's skin.

Korean Patent Laid-Open Publication No. 10-2012-0115486 (Oct. 18, 2012) relates to a curved cannula surgical system in which a robotic surgical system can be configured to have rigid curved cannulas extending through the same opening in a patient's body, and discloses a remote control system that moves curved cannulas and their associated instruments in a manner so that a doctor experiences intuitive control.

SUMMARY

One embodiment of the present invention is to provide an artificial intelligence-based cannula surgery diagnostic device capable of predicting a surgical result based on movement of a cannula and informing a false movement in real time.

One embodiment of the present invention is to provide an artificial intelligence-based cannula surgery diagnostic device, wherein a practitioner can practice while confirming the body information of the person undergoing the surgery (subject), check the depth of the inserted cannula in real time, and perform an accurate and stable operation according to the body shape of the subject.

One embodiment of the present invention is to provide the artificial intelligence-based cannula surgery diagnostic device which can learn the data on past cannula surgery with artificial intelligence, and provide real-time feedback on cannula movement based on this, as well as predict and provide the result of surgery after the surgery is completed.

Among the embodiments, an artificial intelligence-based cannula surgery diagnostic device includes a cannula stroke sensing unit for sensing a stroke of a cannula generated in a surgical procedure of a patient; a surgical data processing unit for receiving surgical data generated based on a stroke of the cannula; and a surgical prognostic information-generating unit for analyzing the received surgical data based on the existing learned surgical data to generate surgical prognostic information for the patient.

The cannula stroke sensing part may sense the reciprocating motion of the stroke through a stroke-sensing sensor mounted on the cannula.

The cannula stroke-sensing unit may calculate the reciprocating path of the stroke.

The surgical data processing unit may receive the input of the puncturing position of the patient before performing the surgery and convert the reciprocating path of the stroke into a surgical path in the body of the patient.

The surgical data processing unit receives the input of the body data obtained through the scan of the patient before performing the surgery, and maps the puncturing position of the patient to the body data.

The surgical data processing unit may calculate a failure probability of the corresponding stroke based on a surgical path in the body of the patient and provide a real time notification when the failure probability exceeds a reference probability.

The surgery prognostic information-generating unit may generate the surgery success probability as the surgical prognostic information by applying the existing learned surgical data to the received surgical data based on the body data.

The surgical prognostic information-generating unit may generate learning data based on the received surgical data and the surgical prognostic information on the patient to update the existing learned surgical data.

DETAILED DESCRIPTION

Figure 1:
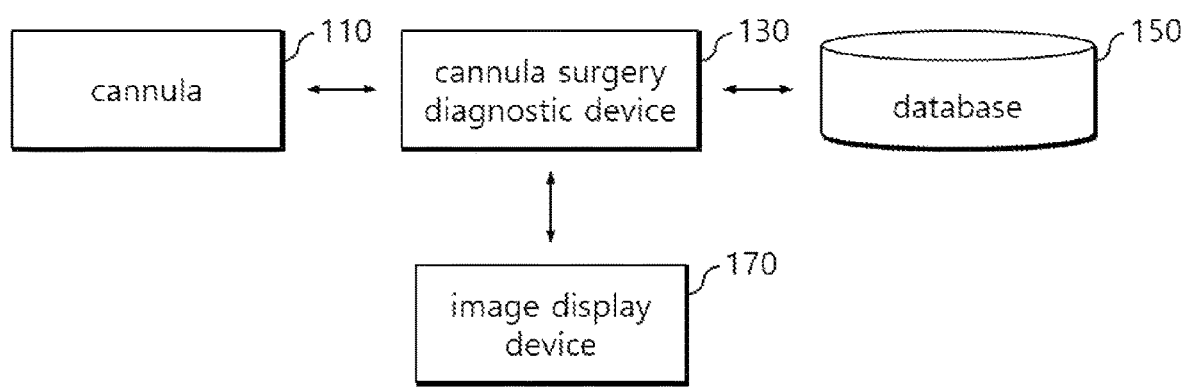
FIG. 1 is a view for explaining an artificial intelligence-based cannula surgery diagnostic system according to one embodiment of the present invention.

The description of the present invention is merely an example for structural or functional explanation, and therefore, the scope of the present invention should not be construed as being limited by the embodiments described in the text. That is, since the embodiments can be variously embodied and have various forms, the scope of the present invention should be understood to include equivalents capable of realizing technical ideas. Also, since the purpose or effect set forth in the present invention is not intended imply that to the specific embodiment, the scope of the present invention should not be construed as being limited thereto.

Meanwhile, the meaning of the terms described in the present application should be understood as follows.

The terms such as "the first", "the second", and the like, are intended to distinguish one element from another, and the scope of the right should not be limited by these terms. For example, the first component may be referred to as the second component, and similarly, the second component may also be referred to as the first component.

It is to be understood that when an element is referred to as being "connected" to other element, it may be directly connected to the other element, but there may also be other elements in between. On the other hand, when an element is referred to as being "directly connected" to other element, it should be understood that there is no other element in between. On the other hand, other expressions that describe the relationship between elements, that is, "between~" and "just between~" or "adjacent to~" and "directly adjacent to~" should be interpreted likewise as well.

The singular expressions should be understood to include plural expressions unless the context clearly dictates otherwise. It is also to be understood that the terms "comprises" or "have", and the like, are to designate the presence of practiced features, numbers, steps, operations, elements, parts, or combinations thereof, but do not preclude the presence or addition, possibility of one or more other features, numbers, steps, operations, elements, parts, or combinations thereof.

In each step, the identification code (e.g., a, b, c, etc.) is used for convenience of explanation, but the identification code does not describe the order of each step, and unless otherwise explicitly stated, it may occur differently from the stated order. That is, each of steps may occur in the same order as described, may also be performed substantially at the same time, and may be performed in reverse order.

The present invention can be embodied as a computer-readable code on a computer-readable recording medium, and the computer-readable recording medium includes all kinds of recording devices for storing data, which can be read by a computer system. Examples of the computer-readable recording medium include ROM, RAM, CD-ROM, magnetic tape, floppy disk, optical data storage device, and the like. In addition, the computer-readable recording medium may be distributed over network-connected computer systems so that computer readable codes can be stored and executed in a distributed manner.

All terms used herein have the same meaning as commonly understood by one of ordinary skill in the art to which this invention belongs, unless otherwise defined. Terms defined in commonly used dictionaries should be interpreted to be consistent with meaning in the context of the related art and cannot be interpreted as having ideal or overly formal meaning unless explicitly defined in the present application.

FIG. 1 is a view for explaining an artificial intelligence-based cannula surgery diagnostic system according to one embodiment of the present invention.

Referring to FIG. 1, an artificial intelligence-based cannula surgery diagnostic system 100 may include a cannula 110, a cannula surgery diagnostic device 130, a database 150, and an image display device 170.

The cannula 110 may correspond to a device that can be inserted into a surgical site corresponding to a patient's body to inhale fat, and the like. The cannula 110 may include thin and long (elongated)-type of tube to be inserted into the body, the top end of the tube is closed, the rear end is opened, and inserted into a surgical site—for example, a fat layer—to move in a forward/backward direction, and the fat cells can be destroyed and the fat cells can be extracted to the outside. The cannula 110 has a top end formed in a streamlined shape to be closed to prevent injury to internal organs or muscles of the body when inserting into a surgical site.

In addition, the cannula 110 corresponds to a medical instrument that allows liquid or air to pass therethrough. The cannula 110 can be used for various purposes such as that it can be inserted into a thoracic cavity or abdominal cavity to extract liquid or insert liquid into the blood vessel so as to draw blood, and it can be inserted into the organ to enable breathing when performing tracheal resection, and the like. The cannula 110 may be embodied in various forms depending on the size, number, and shape of the hole, and may be selected depending on the surgical site and use. The cannula 110 can be connected to the cannula surgery diagnostic device 130 directly or via a network.

The cannula surgery diagnostic device 130 may be embodied as a server corresponding to a computer or program capable of sensing the movement of the cannula 110 in conjunction with the database 150 and providing a diagnosis for the cannula surgery. Here, cannula surgery may correspond to the surgery performed using cannula 110, and may include, for example, liposuction using cannula 110. The cannula surgery diagnostic device 130 may be connected to the cannula 110 and the image display device 170 via a wired network or a wireless network such as Bluetooth, Wi-Fi, etc. and the communication may be performed with the cannula 110 and the image display device 170 via the wired or wireless network.

In one embodiment, the cannula surgery diagnostic device 130 may be coupled with the database 150 to store information necessary for cannula surgery. Meanwhile, unlike FIG. 1, the cannula surgery diagnostic device 130 can be embodied by including the cannula 110, the database 150, or the image display device 170 therein. In addition, the cannula surgery diagnostic device 130 may be embodied by including a processor, a memory, a user input/output unit, and a network input/output unit.

In one embodiment, the cannula surgery diagnostic device 130 may learn a variety of surgical data in advance and construct an artificial intelligence model for cannula surgical diagnosis. The artificial intelligence model can make an analysis for the surgical data collected in the cannula surgery procedure based on the learned results and provide the predicted results of the surgical data as an output. For example, the artificial intelligence model can be constructed by learning patient's body information collected from various liposuction surgeries, information about movement of the cannula 110, and post-surgical progress information. And by analyzing the surgical data collected during the surgical procedure of actual liposuction, it is possible to provide information on the accuracy of the cannula (110)

stroke to be predicted, the probability of success of liposuction, and the like, in real time.

The database 150 may store various informations necessary for the cannula surgery diagnostic device 130 to provide the expected surgical result according to the movement of the cannula. For example, the database 150 may store the generated surgical data by sensing the movement of the cannula 110, and may store the existing learned surgical data for diagnosis of the cannula surgery, and the information collected or processed in various forms can be stored in the process of providing the diagnosis result regarding the cannula surgery, without being necessarily limited thereto.

The image display device 170 may correspond to a display device capable of displaying the diagnosis result of the cannula surgery. The image display device 170 may be embodied as a CRT, LCD, or PDP, but is not necessarily limited thereto and may be embodied by various devices. The image display device 170 may be connected to the cannula surgery diagnostic device 130 via a network and the plurality of image display devices 170 may be connected to the cannula surgery diagnostic device 130 at the same time.

Figure 2:
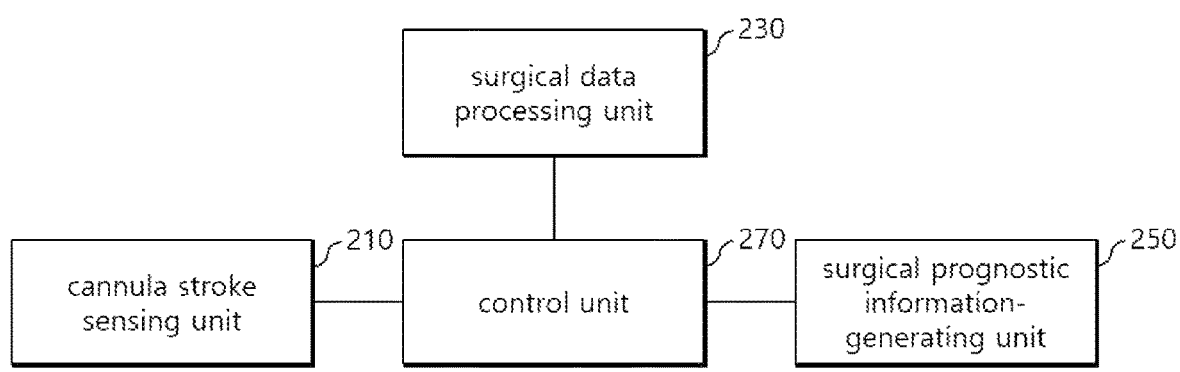
FIG. 2 is a block diagram illustrating the cannula surgery diagnostic device shown in FIG. 1.

FIG. 2 is a block diagram illustrating the cannula surgery diagnostic device of FIG. 1.

Referring to FIG. 2, the cannula surgery diagnostic device 130 may include a cannula stroke sensing unit 210, a surgical data processing unit 230, an operation prognostic information-generating unit 250, and a control unit 270.

The cannula stroke sensing unit 210 can sense a stroke of the cannula 110 generated during the surgical procedure of the patient. The stroke of the cannula 110 may correspond to a unit movement constituting the movement of the cannula 110 repeatedly reciprocating in the forward/backward direction within a constant section as the movement of the cannula 110. That is, the stroke of the cannula 110 may correspond to a single reciprocating movement in the forward/backward direction, and the movement of the cannula 110 may be composed of a plurality of continuous strokes. The cannula stroke sensing unit 210 may receive various data relating to the stroke of the cannula 110 from the cannula 110 and thereby sense the stroke of the cannula 110.

In one embodiment, the cannula stroke sensing unit 210 can sense the reciprocating movement of the stroke through the stroke-sensing sensor mounted on the cannula 110. The cannula stroke sensing unit 210 can communicate with the cannula 110 in a wired or wireless manner and the cannula 110 can sense movement of the cannula 110 through the stroke-sensing sensor. The stroke-sensing sensor may include various motion sensing sensors as a sensor capable of measuring data relating to the stroke of the cannula 110. The stroke-sensing sensor may be embodied with only a single sensor or a plurality of sensors.

The stroke-sensing sensor may include a displacement sensor, an angle sensor, a gyro sensor, and the like. A displacement sensor corresponds to a sensor capable of measuring the distance or position of movement of an object and an angle sensor corresponds to a sensor capable of measuring a relatively large angle such as a fine angle or a rotation angle of an axis, and a gyro sensor may correspond to a sensor capable of detecting the angular velocity. The plurality of sensors included in the stroke-sensing sensor can collect sensing information in real time or periodically according to respective sensing mechanisms, and the cannula surgery diagnostic device 130 may store the sensing signals collected from the plurality of sensors in the database 150 in association with the patient.

In one embodiment, the cannula stroke sensing unit 210 can calculate the reciprocating path of the stroke. The cannula stroke sensing unit 210 can sense the reciprocating movement of the stroke through the stroke-sensing sensor and calculate the reciprocating path of the stroke based on the sensing signal related to the reciprocating movement. For example, the cannula stroke sensing unit 210 may collect various sensing signals through the stroke sensing sensor of the cannula 110, and based on the sensing signal, information such as distance, velocity, angle, etc., can be obtained as information on the stroke of the cannula 110.

Further, the cannula stroke sensing unit 210 can calculate the reciprocating distance, the reciprocating angle, the reciprocating direction, etc. of the stroke on the basis of the obtained various information, and can calculate the reciprocating path of the stroke based on this. The reciprocating path of the stroke may be represented by the reciprocating distance and the reciprocal direction for the unit movement in which the cannula 110 repeatedly reciprocates in the forward/backward direction, and the reciprocating distance may include information on the distance of the repetitive interval and the repetition time, and the reciprocating direction may include information on the advancing angle and speed as the forward/backward direction of the stroke.

The surgical data processing unit 230 may receive the surgical data generated based on the stroke of the cannula 110. The surgical data may be generated based on information regarding movement of the cannula 110 as information related to the patient's surgery and used for cannula surgical diagnosis. For example, the surgical data may be generated by including information regarding distance, velocity, angle, intensity, etc. with respect to movement of the cannula 110. The cannula stroke sensing unit 210 can sense the stroke of the cannula 110 and the sensed data can be transmitted to the surgical data processing unit 230. In another embodiment, the cannula stroke-sensing unit 210 may be embodied by including it inside the cannula 110. When the cannula 110 is wirelessly connected to the cannula surgery diagnostic device 130, the cannula stroke sensing unit 210 can transmit data to the surgical data processing unit 230 through wireless communication.

In one embodiment, the surgical data processing unit 230 receives the puncturing position of the patient before performing the surgery, and may convert the reciprocating path of the stroke into the surgical path in the patient's body. Here, the perforation position may correspond to the position where the cannula 110 is inserted into the body. The surgical data processing unit 230 can receive the puncturing position of the patient from the doctor performing the surgery. For example, the doctor directly touches the insertion position on the patient's body data displayed on the image display device 170, and thus, the puncturing position can be input. In addition, the surgical data processing unit 230 is not necessarily limited to this, and it is possible to input the puncturing position of the patient through various input methods.

More specifically, the surgical data processing unit 230 can perform the conversion to the surgical path that is performed on the actual patient by aligning the reciprocating path of the stroke on the basis of the puncturing position mapped on the patient's body data. The cannula surgery diagnostic device 130 can display the surgical path converted by the surgical data processing unit 230 through the image display device 170, and by displaying them in sequence depending on how time flows, the progress of the operation can be expressed as an image.

In one embodiment, the surgical data processing unit 230 can receive the input of the body data obtained through the scan of the patient before performing the surgery, and map the perforation position of the patient to the body data. The cannula surgery diagnostic device 130 can scan the patient's body through an external scanning device, and the acquired body data can correspond to two-dimensional or three-dimensional data and can be stored in the database 150. The surgical data processing unit 230 may calculate the surgical path in which the stroke of the cannula 110 sensed by the cannula stroke sensing unit 210 is performed on the actual patient by mapping the puncturing position on the patient's body data.

In one embodiment, the surgical data processing unit 230 may calculate the failure probability of the corresponding stroke based on the surgical path in the patient's body and provide a real-time notification if the failure probability exceeds the reference probability. The surgical data processing unit 230 can calculate the failure probability for each stroke based on the body information of the patient and the surgical path by the stroke of the cannula 110. The failure probability of the stroke can be calculated based on the difference between the appropriate stroke range at the perforation position on the basis of the patient's body data. The surgical data processing unit 230 can compare the failure probability with the reference probability, and the reference probability can be set in advance by the cannula surgery diagnostic device 130.

In addition, when the failure probability exceeds the reference probability, the surgical data processing unit 230 can notify it to the doctor performing the surgery in real time. For example, it is possible to notify the failure of the stroke of the cannula 110 in various manners, such as vibration of the cannula 110, playback of the attention image of the image display device 170, playback of the attention music through a separate speaker, and the like.

In one embodiment, the surgical data processing unit 230 may collect surgical pathways within the patient's body for a unit time and may calculate the ratio of the number of failure strokes to the total numbers of strokes collected during that unit time. The failure stroke may correspond to a stroke in which the failure probability of the stroke exceeds the reference probability. The surgical data processing unit 230 may determine the surgical result to be one of a plurality of predetermined success stages based on the corresponding ratio.

For example, the surgical data processing unit 230 may calculate a ratio of 200/1000=0.2 when the total number of strokes collected during the surgical progress is 1000 and the number of failure strokes is 200, and it is possible to determine as the surgery success stages of the four stages out of the five predetermined stages. The success stage of the surgery can be composed of 1 to 5 stages, and the higher the stage, the more likely the operation will fail. Therefore, it can be determined that when 200 strokes are generated among 1000 strokes, the surgery success stage may correspond to the fourth stage, and the corresponding surgery may be determined as that the failure possibility is high.

The surgical prognostic information-generating unit 250 may analyze the received surgical data based on the existing learned surgical data to generate surgical prognostic information for the patient. The surgery prognostic information-generating unit 250 may analyze the surgical data using the artificial intelligence model generated through the machine learning. And, the artificial intelligence model may correspond to the existing learned surgical data, and may be stored in the database 150. The surgical prognostic information-generating unit 250 may generate surgical prognostic information for the patient by analyzing the surgical data and the surgical data may be generated based on information about the stroke of the cannula 110. The surgical prognostic information may include the liposuction amount, the prediction of the body change, the expected recovery period, the probability of operation success, etc., as predicted results for the cannula (110) operation.

In one embodiment, the surgical prognostic information-generating unit 250 may generate the success probability of the surgery as the surgical prognostic information by applying the existing learned surgical data to the surgical data received based on the body data. The cannula surgery diagnostic device 130 can classify the patient's body data into a plurality of predefined types, and can separately construct learning data for each classification. The surgery prognostic information-generation unit 250 can determine the most similar type of learning data according to the patient's body data and analyze the patient's surgical data based on the learning data.

For example, the surgical prognostic information-generating unit 250 may generate an input vector to be input to the artificial intelligence model based on the patient's surgical data, and the surgical prognostic information can be generated based on the results output by the artificial intelligence model. The artificial intelligence model can output the success probability for the relevant surgery as the prediction results and the surgical prognostic information-generating unit 250 can generate the success probability for the operation as the surgery prognostic information.

In one embodiment, the surgical prognostic information-generating unit 250 may generate learning data based on the received surgical data and surgical prognostic information for the patient, and may update the existing learned surgical data. The surgical prognostic information-generating unit 250 may generate information on the stroke of the cannula 110 received during the surgical procedure, the surgical path according to the reciprocating path and the puncturing position for each stroke, and the surgical prognostic information predicted through the artificial intelligence model, and the existing artificial intelligence model can be updated by learning the corresponding learning data. For example, the learning data may be generated by including the predicted surgical prognostic information corresponding to the patient's body information and the stroke information of the cannula 110, and including the predicted surgical success probabilities corresponding to the stroke information of the cannula 110 and the surgical path for each stroke, but are not necessarily limited thereto, and including predictable information in consideration of various factors.

In one embodiment, the surgical prognostic information-generating unit 250 may generate at least one of the liposuction amounts, the degree of body change, and the post-surgical procedure-management data as the prognostic information based on the patient's body data acquired through the scan. For example, when the surgery is terminated, the surgical prognostic information-generating unit 250 can reflect the surgical data on the patient's body data and generate the surgical prognostic information such that 'liposuction of the patient A was completed, and the extracted fat amount of the patient A is 2000 cc, and the reduced circumference of the thigh is 2 cm (12% reduction), and the probability of surgical success is 80%'. In addition, together with this, the information can be generated that 'the expected recovery period according to this is expected as about 4 weeks when the recovery program—B is carried out, and please check the drugs and prohibitions to be cautious'.

The control unit 270 can control the overall operation of the cannula surgery diagnostic device 130, and manage the control flow or data flow between the cannula stroke sensing unit 210, the surgical data processing unit 230 and the surgical prognostic information-generating unit 250.

Figure 3:
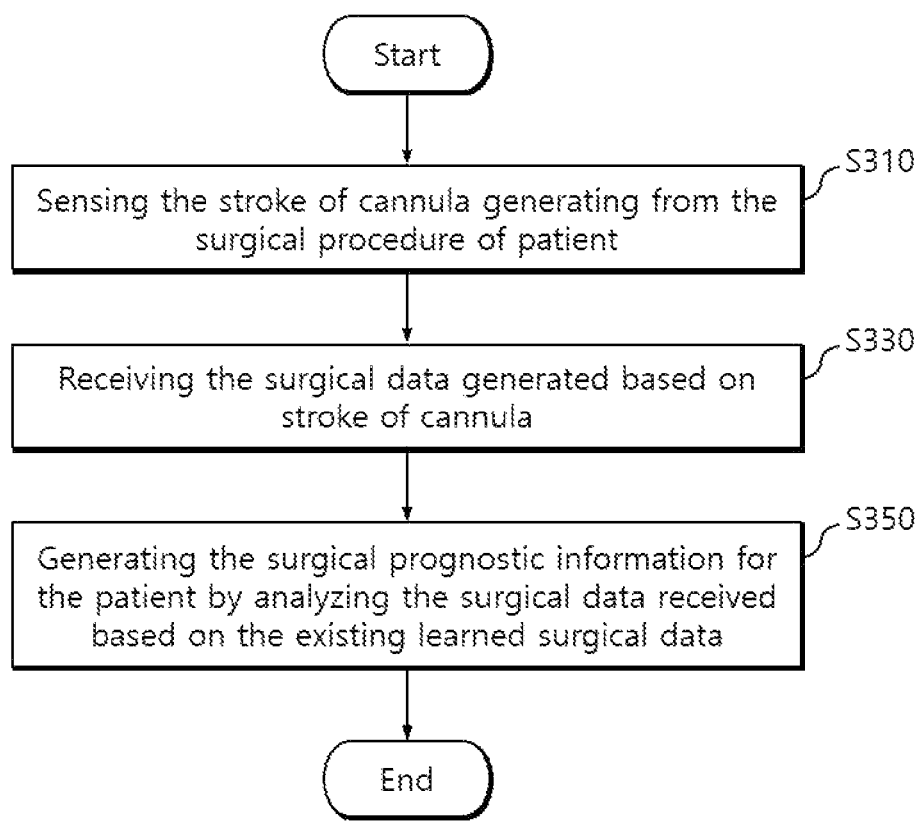
FIG. 3 is a flow chart illustrating a diagnostic procedure for cannula surgery to be performed in the cannula surgery diagnostic device shown in FIG. 1.

FIG. 3 is a flow chart illustrating a diagnostic procedure for the cannula surgery to be performed in the cannula surgery diagnostic device as shown in FIG. 1.

Referring to FIG. 3, the cannula surgery diagnostic device 130 can sense the stroke of the cannula 110 generated during the surgical procedure of the patient through the cannula stroke sensing unit 210 (step S310). The cannula surgery diagnostic device 130 can receive the surgical data generated based on the stroke of the cannula 110 through the surgical data processing unit 230 (step S330). The cannula surgery diagnostic device 130 may analyze the received surgical data based on the surgical data previously learned through the surgical prognostic information-generating unit 250 to generate the surgical prognostic information for the patient (step S350).

Figure 4:
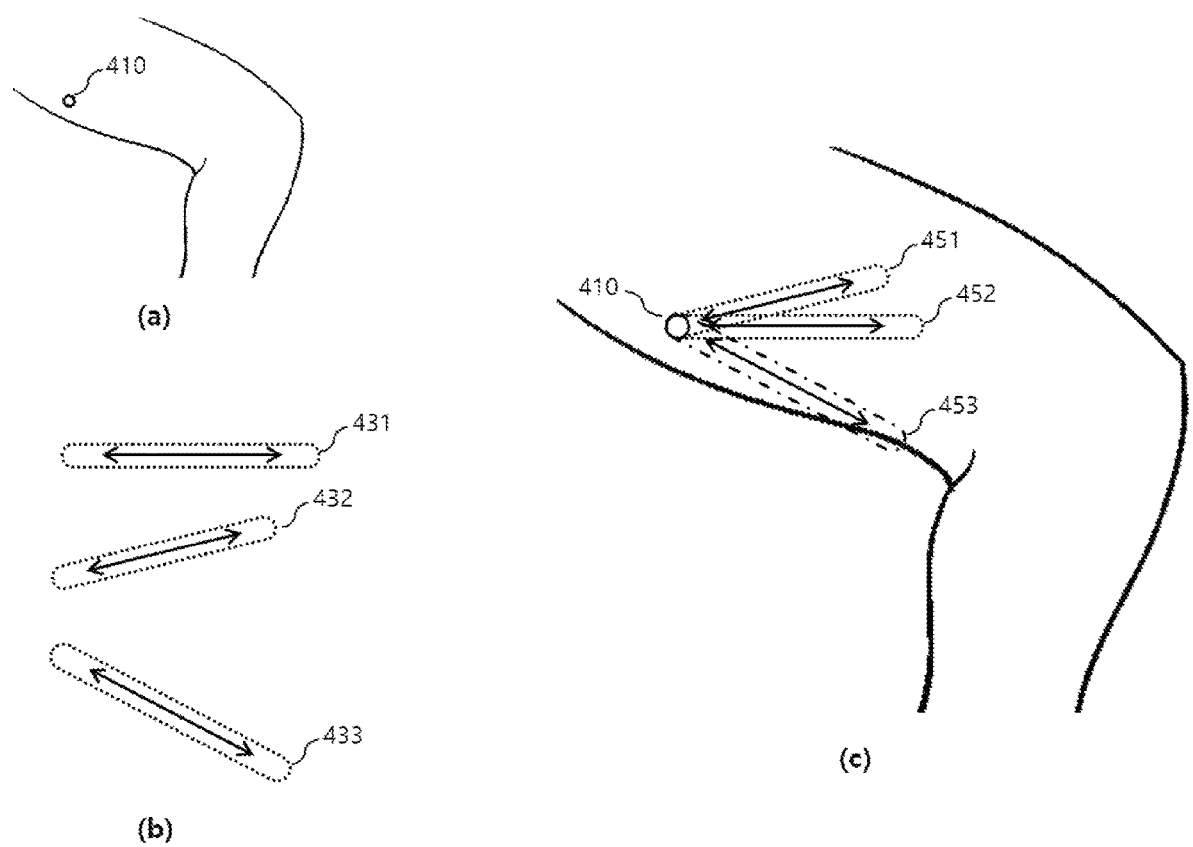
FIG. 4 is an exemplary view illustrating one embodiment in which the surgical data processing unit shown in FIG. 2 processes surgical data.

FIG. 4 is an exemplary view illustrating one embodiment in which the surgical data processing unit in FIG. 2 processes surgical data.

Referring to FIG. 4, the cannula surgery diagnostic device 130 may receive surgical data generated based on the stroke of the cannula 110 through the surgical data processing unit 230. In one embodiment, the surgical data processing unit 230 may receive the patient's puncturing position 410 and body data prior to performing the cannula surgery, and may map the patient's puncturing position 410 to body data. In drawing (a), the surgical data processing unit 230 receives an input for the puncturing position 410 on the thigh image displayed on the image display device 170 when the surgical site corresponds to the thigh, and therefore, the information on the puncturing position 410 can be obtained. The surgical data processing unit 230 may map the thigh of the patient and the puncturing position 410 and display the same through the image display device 170.

Further, the surgical data processing unit 230 may convert the reciprocating paths 431~433 of strokes into the surgical paths 451~453 in the body based on the puncturing position 410 of the patient. More specifically, the surgical data processing unit 230 may convert the reciprocating path of the stroke into the surgical path in the body by aligning the start points of the reciprocating paths 431 to 433 of plurality of strokes sensed through the cannula stroke sensing unit 210 to match the puncturing position 410 of the patient. In drawing (c), a surgical path 453 out of the normal range of the surgical site among the plurality of surgical paths 451~453 converted by the surgical data processing unit 230 may occur. In this case, the surgical data processing unit 230 can notify in real time that a stroke of the cannula 110 having a high probability of failure has occurred, and thus can call attention to the cannula surgery.

Although the present invention has been described with reference to preferred embodiments thereof, it will be understood by those skilled in the art that various modifications and alternations may be made therein without departing from the spirit and scope of the invention as defined in the following claims.

The disclosed technique may have the following effects. Provided that, since it is not meant to imply that a particular embodiment should include all of the following effects or only the following effects, the scope of the disclosed technology is not to be construed as limited thereby.

The artificial intelligence-based cannula surgery diagnostic device according to one embodiment of the present invention can perform the surgery while confirming the body information of the person undergoing surgery and can check the depth of the inserted cannula in real time, and thus, an accurate and highly stable operation can be performed according to the body shape of the person undergoing surgery.

The artificial intelligence-based cannula surgery diagnostic device according to one embodiment of the present invention can learn the data on past cannula surgery with artificial intelligence, and provide real-time feedback on cannula movement based on this, as well as predict and provide the result of surgery after the surgery is completed.

Description of Symbol

| | |
|---|---|
| 100: | artificial intelligence-based cannula surgery diagnostic system |
| 110: | cannula |
| 130: | cannula surgery diagnostic device |
| 150: | database |
| 170: | image display device |
| 210: | cannula stroke sensing unit |
| 230: | surgical data processing unit |
| 250: | operation prognostic information-generating unit |
| 270: | control unit |
| 410: | puncturing position |
| 431~433: | reciprocating path |
| 451~453: | surgical path |

What is claimed is:

1. An artificial intelligence-based cannula surgery diagnostic device, comprising
   a cannula stroke sensing unit for sensing a stroke of a cannula generated in a surgical procedure of a patient;
   a surgical data processing unit for receiving surgical data generated based on a stroke of the cannula; and
   a surgical prognostic information-generating unit for analyzing the received surgical data based on the existing learned surgical data to generate surgical prognostic information for the patient,
   wherein the surgical data processing unit is that the puncturing position of the patient is input before the operation is performed and the reciprocating path of the stroke is converted into a surgical path in the body of the patient, and
   wherein the surgical data processing unit is that a failure probability of the stroke is calculated based on a surgical path in the body of the patient and a real-time notification is provided when the failure probability exceeds a reference probability.

2. The artificial intelligence-based cannula surgery diagnostic device of claim 1, wherein the cannula stroke-sensing unit is that a reciprocating movement of the stroke is sensed through a stroke sensing sensor mounted on the cannula.

3. The artificial intelligence-based cannula surgery diagnostic device of claim 2, wherein the cannula stroke-sensing unit calculates the reciprocating path of the stroke.

4. The artificial intelligence-based cannula surgery diagnostic device of claim 1, wherein the surgical data processing unit is that the body data obtained through the scan of the patient is input before performing the surgery and the puncturing position of the patient is mapped to the body data.

5. The artificial intelligence based cannula surgery diagnostic device of claim 1, wherein the surgical prognostic information-generating unit is that the existing learning data is generated based on the received surgical data, and the surgical prognostic information on the patient, and thus the existing learned surgical data are updated.

6. An artificial intelligence-based cannula surgery diagnostic device, comprising
   a cannula stroke sensing unit for sensing a stroke of a cannula generated in a surgical procedure of a patient;

a surgical data processing unit for receiving surgical data generated based on a stroke of the cannula; and a surgical prognostic information-generating unit for analyzing the received surgical data based on the existing learned surgical data to generate surgical prognostic information for the patient, wherein the surgical data processing unit is that the puncturing position of the patient is input before the operation is performed and the reciprocating path of the stroke is converted into a surgical path in the body of the patient, wherein the surgical data processing unit is that the body data obtained through the scan of the patient is input before performing the surgery and the puncturing position of the patient is mapped to the body data, and wherein the surgical prognostic information-generating unit is that the existing learned surgical data is applied to the received surgical data based on the body data to generate a success probability of the surgery as the surgical prognostic information.

* * * * *